US009051581B2

(12) United States Patent
Fang et al.

(10) Patent No.: US 9,051,581 B2
(45) Date of Patent: Jun. 9, 2015

(54) DEFENSE PEPTIDES AGAINST FUNGAL INFECTION AND METHOD OF THEIR USE

(75) Inventors: Zhiwei Fang, Columbia, MO (US); James T. English, Columbia, MO (US); James E. Schoelz, Columbia, MO (US); Francis J. Schmidt, Columbia, MO (US)

(73) Assignee: The Curators of the University of Missouri, Columbia, MO (US)

(*) Notice: Subject to any disclaimer, the term of this patent is extended or adjusted under 35 U.S.C. 154(b) by 152 days.

(21) Appl. No.: 13/098,442

(22) Filed: Apr. 30, 2011

(65) Prior Publication Data
US 2011/0271400 A1 Nov. 3, 2011

Related U.S. Application Data

(60) Provisional application No. 61/330,173, filed on Apr. 30, 2010.

(51) Int. Cl.

| | |
|---|---|
| *C12N 15/82* | (2006.01) |
| *C07K 7/08* | (2006.01) |
| *C12N 9/02* | (2006.01) |

(52) U.S. Cl.
CPC .............. *C12N 15/8282* (2013.01); *C07K 7/08* (2013.01); *C07K 2319/00* (2013.01); *C07K 2319/735* (2013.01); *C12N 9/0004* (2013.01)

(58) Field of Classification Search
None
See application file for complete search history.

(56) References Cited

U.S. PATENT DOCUMENTS

| | | | |
|---|---|---|---|
| 5,981,840 | A | 11/1999 | Zhao et al. |
| 6,822,144 | B1 | 11/2004 | Zhao et al. |
| 7,700,831 | B2 | 4/2010 | English et al. |
| 2004/0031072 | A1* | 2/2004 | La Rosa et al. |
| 2008/0184393 | A1 | 7/2008 | Zhang et al. |
| 2010/0071089 | A1 | 3/2010 | Frank et al. |

OTHER PUBLICATIONS

Uniprot. 2005. Uniprot Accession No. Q47M31. p. 1-2.*
Macros et al. 2008. Identification and rational design of novel antimicrobial peptides for plant protection. Annu. Rev. Phytopathol. 46:273-301.*
Hillier et al., Sequence and comparative analysis of the chicken genome provide uniquel-25 perspectives on vertebrate evolution; Nature, 2004, vol. 432, pp. 695-716.
Ward et al., "The Genome Sequence of *Bacteroides* sp. strain 2_2_4." (Jun. 2009) C3QQYO_9BACE Submitted (Dec. 2008) to the EMBUGenBankIDDBJ databases [online]. [Retrieved Jan. 16, 2012]. Retrieved from the Internet at URL: http://www.uniprot.org/uniprotIC3QQYO.txt?version=1>. peptide sequence residues 208-217.
PCT/US 11134705, International Search Report & Written Opinion dated Feb. 3, 2012, 10 pages.

Bilyeu, et al., Molecular and biochemical characterization of a cytokinin oxidase from maize, Plant Physiol., 125:378-386 (2001).
Bishop-Hurley, et al., Phage-displayed peptides as developmental agonists for Phytophthora capsici zoospores, Appl. Env. Microbiol., 68:3315-3320 (2002).
Bishop-Hurley, et al., Peptides selected for binding to a virulent strain of *Haemophilus injluenzae* by phage display are bactericidal, Antimicrob. Agents Chemotherapy, 49:2972-2978 (2005).
Bonde, et al., Effects of temperature on urediniospore germination, germ tube growth, and initiation of infection in soybean by Phakopsora isolates, Phytopathology, 97 :997-1003 (2007).
Bonde, et al., Histology of the suscept pathogen relationship between *Glycine max* and *Phakopsora pachyrhizi*, the cause of soybean rust, Phytopathology, 66:1290-1294 (1976).

Christiano, R. S. C., and Scherm, H., Quantitative aspects ofthe spread of Asian soybean rust in the southeastern United States, 2005 to 2006, Phytopathology, 97:1428-1433 (2007).

Fang, et al., Combinatorially selected defense peptides protect plant roots from pathogen infection, PNAS 103:18444-18449 (2006).

Hartman, et al., Breeding for resistance to soybean rust, Plant Dis. 89:664-666, (2005).

Isard, et al., The effect of solar irradiance on the mortality of *Phakopsora pachyrhizi* urediniospores, Plant Dis., 90:941-945 (2006).

Jurick, et al., Winter survival ofthe soybean rust pathogen, *Phakopsora pachyrhizi*, in Florida, Plant Dis., 92:1551-1558 (2008).

Krupa, et al., Introduction of Asian soybean rust urediniospores into the Midwestern United States—a case study, Plant Dis., 90:1254-1259 (2006).

Lygin, et al., The importance of phenolic metabolism to limit the growth of *Phakopsora pachyrhizi*. Phytopathology, 99:1412-1420 (2009).

Marchetti, M. A., Uecker, F. A., and Bromfield, The effects oftemperature and dew period on germination and infection by uredospores of *Phakopsora pachyrhizi*,. Phytopathology, 66:461-463, (1976).

Melching, et al., Effects of duration, frequency, and temperature of leaf wetness periods on soybean rust, Plant Dis., 73:117-122 (1989).

Miles, et al., International fungicide efficacy trials for the management of soybean rust. Plant Dis., 91: 1450-1458 (2007).

Miles, et al., Differential response of common bean cultivars to *Phakopsora pachyrhizi*. Plant Dis., 91 :698-704 (2007).

(Continued)

*Primary Examiner* — Medina A Ibrahim

*Assistant Examiner* — Steven Bernacki

(74) *Attorney, Agent, or Firm* — Thompson Coburn LLP; J. Wendy Davis; Steven M. Ritchey

(57) ABSTRACT

*Phakopsora pachyrhizi*, the fungal pathogen that causes Asian soybean rust, has the potential to cause significant losses in soybean yield in many production regions of the U.S. To assist the development of new modes of soybean resistance to fungal infection, peptides were identified from combinatorial phage-display peptide libraries which inhibit germ tube growth from urediniospores of *P. pachyrhizi*. Two peptides, Sp2 and Sp39, were identified that inhibit germ tube development when displayed as fusions with the coat protein of M13 phage or as fusions with maize cytokinin oxidase/dehydrogenase (ZmCKX1). These peptides may be used in vitro to help control fungal infection. These peptides may also be expressed as transgenes in a plant to help the resulting transgenic plant defend against the fungi.

23 Claims, 5 Drawing Sheets

(56) References Cited

OTHER PUBLICATIONS

Mortel, M., et al., Distinct biphasic mRNA changes in response to Asian soybean rust infection, Mol. Plant-Microbe Interact., 20:887-899, (2007).

Mueller, T. A., et al., Effect of fungicide and timing of application on soybean rust severity and yield, Plant Dis., 93:243-248, (2009).

Pimental, D., et al., Update on the environmental and economic costs associated with alien-invasive species in the United States, Ecol. Econ., 52:273-288 (2005).

Pivonia, S., and Yang, X. B., Assessment of the potential year-round establishment of soybean rust throughout the world. Plant Dis., 88:523-529, (2004).

Pivonia, S., and Yang, X. B., Assessment of epidemic potential of soybean rust in the United States, Plant Dis., 89:678-682 (2005).

Posada-Buitrago, M. L., and Frederick, R. D., Expressed sequence tag analysis of the soybean rust pathogen, *Phakopsora pachyrhizi*, Fungal Gen. Biol., 42:949-962 (2005).

Rossman, A. Y., The impact of invasive fungi on agricultural ecosystems in the United States, Biol. Invasions, 11:7-101 (2009).

Schneider, et al., First report of soybean rust caused by *Phakopsora pachyrhizi* in the continental United States, Plant Dis., 89:774 (2005).

\* cited by examiner

DEFENSE PEPTIDES AGAINST FUNGAL INFECTION AND METHOD OF THEIR USE

RELATED APPLICATIONS

This application claims benefit of priority to U.S. Provisional Patent Application Ser. No. 61/330,173, filed Apr. 30, 2010, the contents of which are hereby incorporated by reference.

SEQUENCE LISTING

This application is accompanied by a sequence listing in a computer readable form that accurately reproduces the sequences described herein.

BACKGROUND

I. Field of the Invention

This disclosure relates to the use of anti-fungal peptides as defense against plant pathogens such as *Phytophthora*, *Phakapsora*, and *Uromyces*. This disclosure also relates to transgenic plants expressing such anti-fungal peptides.

II. Description of the Related Art

Invasive plant pathogens present a constant challenge to the agricultural economy. The impact of invasive pathogens in terms of crop loss and management costs is estimated at $23.5 billion annually in the U.S. (26). Among the most significant invasive pathogens are fungi and oomycetes. Invasive fungal species are difficult to detect because they may be hiding in plant tissues that are distributed or commercially exchanged. See Rossman (30). The extreme diversity of fungi and the lack of comprehensive taxonomic description also make it difficult to rapidly identify, diagnose, and mitigate fungal infection.

*Phakopsora pachyrhizi* is a fungus that may cause the rust disease of soybean (*Glycine max*), also known as Asian Soybean Rust. This pathogen has spread from Asia to all other major soybean production regions in the world. *P. pachyrhizi* arrived in the U.S. during the fall of 2004. At present, there is no known durable resistance available in any soybean varieties. *Uromyces appendiculatus* is a fungus that causes rust on bean (*Phaseolus vulgaris*), among others.

As rust-inducing fungi, *U. appendiculatus* and *P. pachyrhizi* belong to the order Uredinales, within the class Basidiomycetes. *U. appendiculatus* produces five spore stages on a single host plant. *P. pachyrhizi* reproduces predominantly by uredospores on a single host plant. Uredospores are responsible for rapid spread of the fungus. *P. pachyrhizi* can infect dozens of legume species, in addition to soybean.

Uredospores of *U. appendiculatus* typically penetrate through foliar stomatal openings, while germinated uredospores of *P. pachyrhizi* usually penetrate directly through the leaf epidermal cell layer. A urediniospore that lands on the surface of a soybean leaf germinates to produce a germ tube that, in turn, produces an appressorium and penetration hypha. As is typical for biotrophic pathogens, further colonization of tissues occurs within the apoplast, with haustorium formation occurring intracellularly (5, 12, 13).

*P. pachyrhizi* can infect almost any cultivar that have been tested so far. No durable, natural resistance to rust has been found in more than 18,000 soybean varieties. Breeders have been trying to identify genes in soybean or bean that can be manipulated to confer rust resistance. Despite extensive research, no durable single-gene resistance to Asian soybean rust has been discovered (8).

SUMMARY

The presently disclosed instrumentalities overcome some of the problems outlined above and advance the art by providing methods for generating plants that are more resistant to fungal infection. In one embodiment, soybean plants may be rendered less susceptible to soybean rust. In another embodiment, the same general techniques may render *Phaseoulus vulgaris* more resistant to common rust.

It is disclosed here a method for selecting peptides that may inhibit the grow and/or colonization of fungi in a plant. Because of the difficulty in selecting peptides against colonizing hyphae and haustoria, an alternative strategy is developed focusing on the elongating urediniospore germ tubes as a surrogate cellular target for peptide selection. It is disclosed here peptides from combinatorial libraries that bind and inhibit *P. pachyrhizi* germ tube development. These peptides may be called "defense peptides," or "plant defense peptides" in this disclosure. In another aspect, potential targets on the pathogens that may interact with the peptides are also disclosed.

In one embodiment, a method for identifying peptides having an affinity for the surface of a plant pathogen is disclosed. In this method, a library is constructed to include random peptides by providing degenerate oligonucleotides encoding peptides. The oligonucleotides are inserted into an appropriate vector that expresses the encoded peptides on its surface and is capable of transfecting a host cell. A host cell is transfected with the vector to amplify the vector in an infectious form to create a library of peptides on the vector. The vector expressing the peptide library is then contacted with a target pathogen and allowed to bind to the pathogen. Unbound vector is removed and vector that has bound to the pathogen eluted. The eluted vector is then amplified in a suitable host cell and the inserted oligonucleotides are isolated. The oligonucleotides are then sequenced and the amino acid sequences of the encode peptides may be deduced from the sequence of the oligonucleotides.

In one aspect, the peptides of the present disclosure may be identified and selected without any knowledge of specific pathogenicity targets in the pathogen. Since these peptides do not necessarily occur in plants in nature, the pathogen likely has not been exposed to these peptides before. Consequently, these peptides deployed in plants may be more effective across a broader spectrum of pathogens, and the efficacy is likely more long lasting as compared to other peptides.

Traditional methods of phage-display peptide selection are based on panning of libraries against purified molecules of specific interest, for example as shown in Barbas et al., 2001. The present methodology differs from previous techniques in that library screening against whole-cells does not require prior knowledge of a specific target or high concentrations of the purified target molecule.

In one aspect, the disclosed peptides may provide rust resistance in transformed plants when displayed as part of scaffold proteins. In another aspect, the peptides may be selected according to the instrumentalities disclosed herein by binding affinity for infective structures of germlings, i.e., germinated spores, of *U. appendiculatus* or *P. pachyrhizi*. This binding affinity may inhibit further development and pathogenesis of the spores. The peptides are, accordingly, shown to inhibit pathogenesis of these fungi. In another aspect, cytokinin oxidase may be used as a scaffold protein for display of selected peptides in plants.

Over time, pathogen populations may be able to adapt to the presence of a selected resistance-conferring peptide. However, new defense peptides may be selected rapidly to meet the challenge of changing pathogen populations. One of the advantages of the disclosed instrumentalities include the speed and simplicity of peptide selection process and phenotype assessment. In one embodiment, peptide selection according to the instant disclosure does not required knowledge of pathogenicity targets in a pathogen. In another embodiment, the methodology may provide a high percentage of recovery of effective peptides, an ability to rapidly identify new defense peptides on demand, an ability to deploy scaffold-peptides to susceptible plant tissues, and an ability to modify scaffold-peptide constructs rapidly on demand.

In one embodiment, an antifungal composition may contain a protein, wherein the protein may contain as a fragment a peptide having an amino acid sequence that is identical to SEQ ID No. 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or combination thereof may be used.

In another embodiment, a polynucleotide containing a first DNA fragment is provided. The first DNA fragment encodes a first polypeptide having an amino acid sequence selected from the group consisting of SEQ ID No. 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and combination thereof.

In another embodiment, the polynucleotide may further contain a second DNA fragment encoding a second polypeptide, wherein the second polypeptide may be expressed in the same molecule as the first polypeptide when the polynucleotide is expressed in a plant, and the second polypeptide facilitates the presentment of the first polypeptide to a pathogen that invades the plant. Examples of the second polypeptide may include but are not limited to scaffold proteins, such as cytokinin oxidase (CKX) from certain plants.

By way of illustration, cytokinin oxidase (CKX) may be used as a peptide-delivery scaffold. A member of the CKX family derived from maize (Morris, 1997) may, for example, be used as a delivery molecule. CKX is endogenously produced, possesses a peptide signal sequence for secretion from cells and is sufficiently glycosolated to provide stability in the presence of proteolytic enzymes in the intercellular region (Morris et al., 1999). Based on the known three-dimensional structure of CKX, as reported by Malito et al., 2004, CKX may be engineered to display peptides at an exposed C-terminus. Other proteins that are typically presented onto the cell surface or secreted outside the cells may also be used as scaffold proteins.

The polynucleotide may be cloned into an expression vector, which may further contain a promoter to control expression of the polynucleotide. The vector may be introduced into a cell, a plant, a fungus, or a bacterium. By way of example, such promoter may be a tissue specific promoter so that the first DNA fragment and the second DNA fragment are expressed in a tissue specific manner when expressed in plants. In one aspect, the promoter is a tissue specific promoter that drives expression only in roots. In another aspect, the promoter is a tissue specific promoter that drives expression only in the leaves.

In one embodiment, the polynucleotide may be introduced into a host plant, by transformation, wherein the polynucleotide contain a first DNA fragment encoding a first polypeptide having an amino acid sequence selected from the group consisting of SEQ ID No. 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and combination thereof. In another embodiment, the host plant is susceptible to infection by a fungus, such as, for example, *Uromyces appendiculatus, Phytophthora capsici,* or *Phakopsora pachyrhizi*. Examples of a host plant may include but are not limited to soybean, bean, corn, wheat, rice, among others.

The transgenic plant is preferably more resistant than the host plant to infection caused by at least one fungus, such as *Uromyces appendiculatus, Phytophthora capsici,* or *Phakopsora pachyrhizi*. More preferably, the transgenic plant is more resistant than the host plant to infection by both *Uromyces appendiculatus* and *Phakopsora pachyrhizi*. As used herein, when a plant is said to be "more resistant" than another plant to a pathogen, it means that when the two plants are exposed to the same pathogen under the same condition, the more resistant plant has significantly fewer incidence of infection by the pathogen than the less resistant one. For purpose of this disclosure, the term "significant" means a difference of at least 30%.

In one embodiment, the transgenic plants thus created may be planted in regions where fungal infection is endemic. In another embodiment, the transgenic plants thus created may be planted in regions where fungal invasion is likely to occur in the near future.

In another embodiment, the defense peptides may be expressed in a host suitable for massive production of relatively large quantity of recombinant proteins. Example of such host include but are not limited to a phage, a yeast cell or a bacterium cell. The peptides may be expressed as stand-alone polypeptides or may be expressed as fusion proteins wherein the defense peptide may be fused with a scaffold protein. Defense peptides thus created may be used in the field to inhibit fungal infection. For instance, the peptides may be sprayed onto plants to help them fight against fungal infection.

In another aspect, the second polypeptide may be a polypeptide that is normally expressed in a plant cell in nature. Preferably, the second polypeptide contains a signal peptide that controls the final destination of the second polypeptide after being expressed in a cell, such as, for example, being presented to the cell surface or being secreted outside the cell. Thus, when the second polypeptide is fused with the defense peptide and expressed in a transgenic plant, the signal peptide may also facilitate the expression of the defense peptide on the cell surface or outside the cell.

BRIEF DESCRIPTION OF THE DRAWINGS

FIG. 1 shows the germ tube development of *Phakopsora pachyrhizi* urediniospores after 8 h incubation in A, water, or when B, mixed with $10^{13}$ virions $ml^{-1}$ of phage-display peptide clone M13-Sp2.

FIG. 2 shows germ tube elongation of *Phakopsora pachyrhizi* urediniospores in relation to concentration of phage-display peptides M13-Sp2 and M13-Sp39, in the presence of the unselected phage-display peptide library (Lib), or in water. Measurements of germ tube elongation were made after 8 h incubation. Bars indicate standard error of the mean (n=4).

FIG. 3 shows germ tube elongation of *Phakopsora pachyrhizi* urediniospores in relation to concentration of ZmCKX1 scaffold-display peptides ZmCKX1-Sp2 and ZmCKX1-Sp39, ZmCKX1 without peptide insert, or in water as controls. Measurements of germ tube elongation were made after 8 h incubation. Bars indicate standard error of the mean (n=4).

FIG. 4 shows time-course development of rust lesions after inoculation of soybean leaves with 50 *Phakopsora pachyrhizi* urediniospores mixed with 10 µl of 115 µM scaffold-display peptides ZmCKX1-Sp2 and ZmCKX1-Sp39, with 115 µM ZmCKX1 without peptide insert, or water as controls.

DETAILED DESCRIPTION

Figure 1:
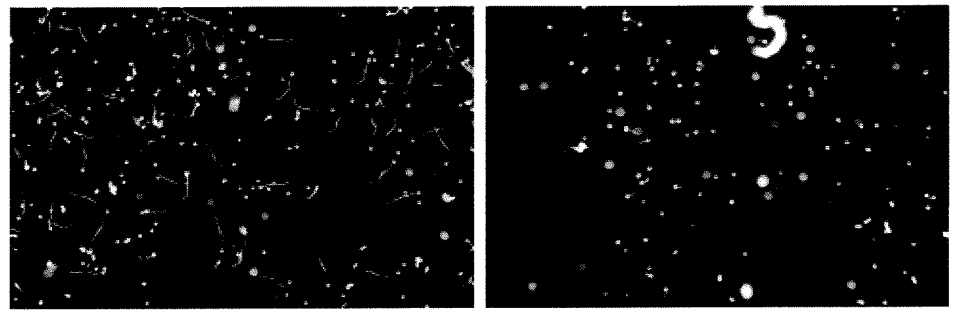

Fungal infection is one of the biggest challenges for farmers and plant breeders. Asian soybean rust is an ongoing problem in the United States. *Phakopsora pachyrhizi* is the causative agent of Asian soybean rust. Although *P. pachyrhizi* is now only endemic in part of the U.S. (11, 27, 28), the pathogen may spread rapidly with shifting weather patterns (6, 14). When *Phakopsora pachyrhizi* was introduced to the U.S., no sustainable single-gene resistance was available in host germplasm collections (8). Consequently, the primary treatment option for Asian soybean rust remains timely application of fungicides (19, 23). Although the impact of rust on soybean production nationally has been lower than initially feared, the establishment of *P. pachyrhizi* in the U.S. provides opportunities for the evolution of environmentally adapted and more virulent populations.

The lack of durable resistance in commercial soybean and related germplasm collections has created a need for alternative modes of protection against rust. Efforts in this regard have focused on elucidation of soybean gene expression patterns (22, 24, 25) as well as metabolic and cell structural changes (16) brought about by pathogen infection, with the intent of identifying critical defense response components.

The data presented here provide a new approach for dealing with invasive pathogens, such as *P. pachyrhizi*. The approach is straightforward, and may include the steps of: (1) identifying infectious stages of the pathogen, (2) finding combinatorially derived peptides that bind to infectious structures and inhibit the pathogen's life cycle, and (3) displaying one or more inhibitory peptides on a suitable carrier (scaffold) protein. The carrier-peptide constructs can then be introduced into transgenic plant lines and screened by conventional assessment methods. This approach roughly parallels the screening approach used in developing biopharmaceuticals for human medicine.

This pharmacological and genetic approach is successful despite complications due to the preparation of pathogen inoculum. Urediniospores could not be produced on artificial growth medium because of the obligate lifestyle of the pathogen. Therefore, infectious urediniospores of *P. pachyrhizi* were obtained from soybean leaves grown in the field or greenhouse in Florida, or under growth chamber conditions in our laboratory. Infection of leaves in the field and greenhouse occurs asynchronously through the course of multiple cycles of pathogen reproduction and secondary infection. As a result, urediniospores produced in these environments were exposed to variable periods of fluctuating solar radiation and temperatures before being harvested for experiments. Previous studies established that the viability of urediniospores is affected significantly by each of these environmental factors (10, 17). Variation in spore viability, inherent to mixed-age spore populations, likely contributed to the phenotypic variability that was observed in initial phage-display peptide assessment experiments. In comparison, urediniospores produced in growth chambers after controlled, synchronous infection of leaves, would be expected to be more uniform in behavior.

Of the peptides that showed inhibition of germ tube growth, peptides Sp2 and Sp39 proved most effective. These bioactive peptides inhibited urediniospore germ tube development in a concentration-dependent manner, and they showed similar efficacy in either phage or scaffold-display formats. In phage-display format, Sp2 and Sp39 maximally inhibited germ tube elongation at $\approx 10^{13}$ virions ml$^{-1}$. Since M13 phage virions display a copy of the Sp2 or Sp39 peptide on each of the five copies of the pIII coat protein, the effective peptide concentration was equivalent to 10 nM. In contrast, when Sp2 or Sp39 were displayed on the ZmCKX1 scaffold, maximum germ tube inhibition was achieved at 115 µM concentration. The $\approx$100-fold difference between effective phage- and scaffold-display peptide concentrations may reflect an avidity effect of multiple peptides being displayed on the phage virion. Alternatively, display of peptides on ZmCKX1 may favor different peptide conformation(s) than display on the phage coat protein, also affecting affinity or activity of the peptides.

The inhibitory peptides may act as temporal inhibitors of urediniospore germination rather than as fungicides. Soybean leaves inoculated with urediniospores mixed with peptides Sp2 and Sp39 in phage or scaffold-display formats developed tan lesions that are characteristic of a susceptible response to infection (8, 20). However, the rate of appearance and final incidence of lesions in the presence of these peptides was notably lower than on leaves inoculated with urediniospores alone. This inhibition is highly significant, because the peptide effects are strongly evident in a one-time exposure of urediniospores to peptides on the surface of leaves. Based on previous studies of ZmCKX1-peptide expression of in tomato hairy roots (7), it is hypothesized that sufficient peptide concentrations can be generated in the apoplast of soybean leaf tissues to inhibit *P. pachyrhizi* hyphal growth and haustorial development.

The application of combinatorial peptide selection against *P. pachyrhizi* provides a means for the rapid discovery of inhibitory peptides. The time from acquisition of *P. pachyrhizi* urediniospores to availability of DNA sequences for plant transformation is about 1.5 person-years, once necessary regulations were satisfied for working with the pathogen. In addition, this combinatorial, pharmacological approach may provide protective determinants limited in number only by the complexity of the phage display library, typically greater than one billion. Such diversity provides many opportunities for identifying peptides that target a range of pathogen functions such as germling growth in *P. pachyrhizi*, the premature encystment of zoospores as in *P. capsici* (2, 7), or some other function critical for pathogen development and pathogenesis.

Figure 7:
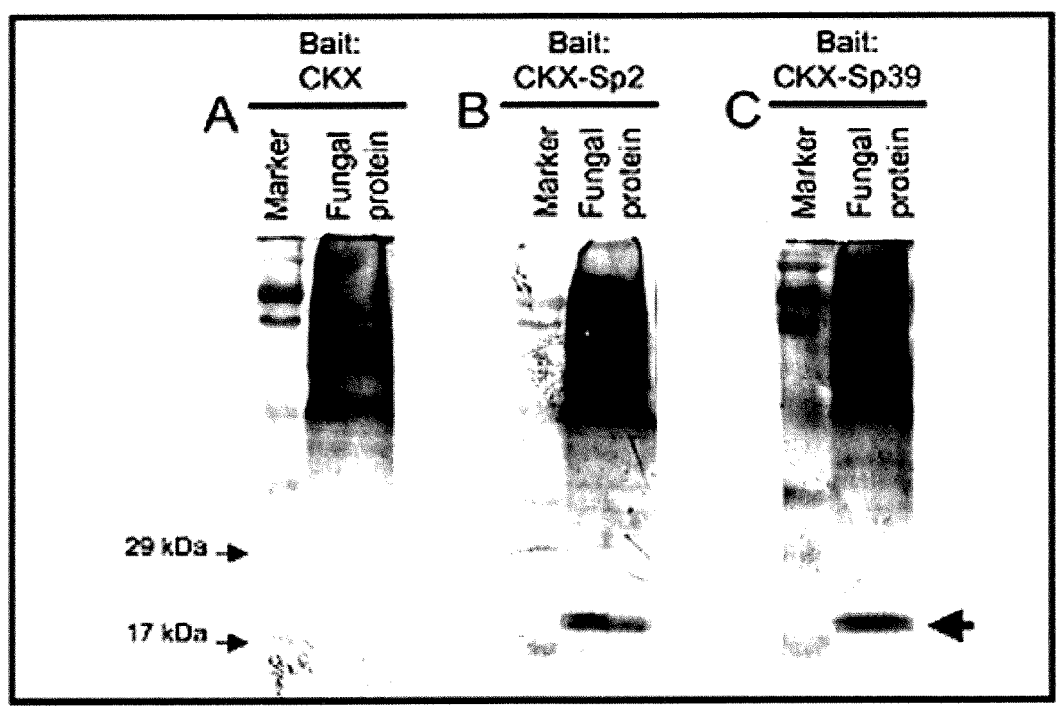
FIG. 7 shows the detection of a 20 kDa *Phakopsora pachyrhizi* protein by peptides Sp-2 and Sp39 using far-western analysis.

The two inhibitory peptides Sp2 and Sp39 detect protein bands that had the same size in far-western blots (FIG. 7). This result illustrates that peptides chosen for their capacity to inhibit a process such as germling growth can also bind to specific pathogen proteins; this presumably would be a prerequisite for determining the inhibitory mode of action of the peptides.

Both the speed of discovery and diversity of inhibitory peptides should be accelerated and enhanced as information on candidate molecular targets accumulate with continuing genomic and proteomic investigations (22, 24, 25, 29). Peptides can be readily selected by in vitro biopanning for their affinity to proteins critical for fungal growth and pathogenesis.

Selection of specific target-peptide interactions also allows the development of inhibitory peptides that are species-specific, as we have observed in a previous study with *P. capsici* (2). This attribute is critical for addressing concerns of potential negative impacts on beneficial, symbiotic fungi and other microbes.

In another aspect, multiple peptides may be identified that have potentially different modes of inhibitory action, and these may be deployed in sequence as effectiveness might be lost in the presence of evolving pathogen populations. Incorporating one or more inhibitory peptides into breeding programs for partial resistance or yield stability (8) may assist the development of new soybean cultivars with enhanced, durable tolerance to rust.

"Secretion sequence" or "signal peptide" refers to a sequence that directs newly synthesized secretory or membrane proteins to and through membranes of the endoplasmic reticulum, or from the cytoplasm to the periplasm across the inner membrane of bacteria, or from the matrix of mitochondria into the inner space, or from the stroma of chloroplasts into the thylakoid. Fusion of such a sequence to a gene that is to be expressed in a heterologous host ensures secretion of the recombinant protein from the host cell.

"Germling" means a newly germinated cyst (5-8 hr post germination) that bears an emergent germ tube. "TBS" means Tris-buffered saline (50 mM Tris-HCl, pH 7.5, 150 mM NaCl). "IPTG" is isopropylthiogalactoside. "TU" means transducing unit. "NAP buffer" is 80 mM NaCl, 50 mM NH4H2PO4, pH adjusted to 7.0 with NH4OH. "NZY-Tc" is a bacterial growth medium containing 1% NZ amine A (a typtone-type medium; Humko-Sheffield Chemical, Norwich, N.Y.), 0.5% yeast extract, 0.5% NaCl, pH 7.0 adjusted with NaOH.

"PCR" means polymerase chain reaction. As used herein "polynucleotide" and "oligonucleotide" are used interchangeably and refer to a polymeric (2 or more monomers) form of nucleotides of any length, either ribonucleotides or deoxyribonucleotides. Although nucleotides are usually joined by phosphodiester linkages, the term also includes polymeric nucleotides containing neutral amide backbone linkages composed of aminoethyl glycine units. This term refers only to the primary structure of the molecule. Thus, this term includes double- and single-stranded DNA and RNA. It also includes known types of modifications, for example, labels, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.), those containing pendant moieties, such as, for example, proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide. Polynucleotides include both sense and antisense strands.

"Sequence" means the linear order in which monomers occur in a polymer, for example, the order of amino acids in a polypeptide or the order of nucleotides in a polynucleotide.

The terms "Peptide," "Protein" and "Polypeptide" are used interchangeably and mean a compound that consists of two or more amino acids that are linked by means of peptide bonds. It is to be recognized that peptide can be modified by chemicals, sugar chains, among others.

"Recombinant protein" means that the protein, whether comprising a native or mutant primary amino acid sequence, is obtained by expression of a gene carried by a recombinant DNA molecule in a cell other than the cell in which that gene and/or protein is naturally found. In other words, the gene is heterologous to the host in which it is expressed. It should be noted that any alteration of a gene, including the addition of a polynucleotide encoding an affinity purification moiety, makes that gene unnatural for the purposes of this definition, and thus that gene cannot be "naturally" found in any cell.

Also within the scope of the disclosed instrumentalities are recombinant oligonucleotides, discovered by the method taught herein, encoding peptides having antifungal activity. These recombinant oligonucleotides can be used to produce recombinant polynucleotides which are commonly used as cloning or expression vectors although other uses are possible. A cloning vector is a self-replicating DNA molecule that serves to transfer a DNA segment into a host cell. The three most common types of cloning vectors are bacterial plasmids, phages, and other viruses. An expression vector is a cloning vector designed so that a coding sequence inserted at a particular site will be transcribed and translated into a protein.

Both cloning and expression vectors contain nucleotide sequences that allow the vectors to replicate in one or more suitable host cells. In cloning vectors, this sequence is generally one that enables the vector to replicate independently of the host cell chromosomes, and also includes either origins of replication or autonomously replicating sequences. Various bacterial and viral origins of replication are well known to those skilled in the art and include, but are not limited to the pBR322 plasmid origin, the 2μ plasmid origin, and the SV40, polyoma, adenovirus, VSV and BPV viral origins.

The oligonucleotide sequences of the present disclosure may be used to produce antifungal peptides by the use of recombinant expression vectors containing the oligonucleotide sequence. Suitable expression vectors include chromosomal, non-chromosomal and synthetic DNA sequences, for example, SV 40 derivatives; bacterial plasmids; phage DNA; baculovirus; yeast plasmids; vectors derived from combinations of plasmids and phage DNA; and viral DNA such as vaccinia, adenovirus, fowl pox virus, and pseudorabies. In addition, any other vector that is replicable and viable in the host may be used.

The nucleotide sequence of interest may be inserted into the vector by a variety of methods. In the most common method the sequence is inserted into an appropriate restriction endonuclease site(s) using procedures commonly known to those skilled in the art and detailed in, for example, Sambrook et al., *Molecular Cloning, A Laboratory Manual,* 2nd ed., Cold Spring Harbor Press, (1989) and Ausubel et al., *Short Protocols in Molecular Biology,* 2nd ed., John Wiley & Sons (1992).

In one embodiment, in an expression vector, the sequence of interest is operably linked to a suitable expression control sequence or promoter recognized by the host cell to direct mRNA synthesis. Promoters are untranslated sequences located generally 100 to 1000 base pairs (bp) upstream from the start codon of a structural gene that regulate the transcription and translation of nucleic acid sequences under their control. Promoters are generally classified as either inducible or constitutive. Inducible promoters are promoters that initiate increased levels of transcription from DNA under their control in response to some change in the environment, e.g. the presence or absence of a nutrient or a change in temperature. Constitutive promoters, in contrast, maintain a relatively constant level of transcription.

A nucleic acid sequence is operably linked when it is placed into a functional relationship with another nucleic acid sequence. For example, DNA for a presequence or secretory leader is operatively linked to DNA for a polypeptide if it is expressed as a preprotein which participates in the secretion of the polypeptide; a promoter is operably linked to a coding sequence if it affects the transcription of the sequence; or a ribosome binding site is operably linked to a coding sequence if it is positioned so as to facilitate translation. Generally, operably linked sequences are contiguous and, in the case of a secretory leader, contiguous and in reading phase. Linking is achieved by ligation at restriction enzyme sites. If suitable restriction sites are not available, then synthetic oligonucleotide adapters or linkers can be used as is known to those skilled in the art. Sambrook et al., *Molecular Cloning, A Laboratory Manual*, 2nd ed., Cold Spring Harbor Press, (1989) and Ausubel et al., *Short Protocols in Molecular Biology*, 2nd ed., John Wiley & Sons (1992).

Common promoters used in expression vectors include, but are not limited to, LTR or SV40 promoter, the *E. coli* lac or trp promoters, and the phage lambda PL promoter. Useful inducible plant promoters include heat-shock promoters (Ou-Lee et al. (1986) *Proc. Natl. Acad. Sci. USA* 83: 6815; Ainley et al. (1990) *Plant Mol. Biol.* 14: 949), a nitrate-inducible promoter derived from the spinach nitrite reductase gene (Back et al. (1991) *Plant Mol. Biol.* 17: 9), hormone-inducible promoters (Yamaguchi-Shinozaki et al. (1990) *Plant Mol. Biol.* 15: 905; Kares et al. (1990) *Plant Mol. Biol.* 15: 905), and light-inducible promoters associated with the small subunit of RuBP carboxylase and LHCP gene families (Kuhlemeier et al. (1989) *Plant Cell* 1: 471; Feinbaum et al. (1991) *Mol. Gen. Genet.* 226: 449; Weisshaar et al. (1991) *EMBO J.* 10: 1777; Lam and Chua (1990) *Science* 248: 471; Castresana et al. (1988) *EMBO J.* 7: 1929; Schulze-Lefert et al. (1989) *EMBO J.* 8: 651). Other promoters known to control the expression of genes in prokaryotic or eukaryotic cells can be used and are known to those skilled in the art. Expression vectors may also contain a ribosome binding site for translation initiation, and a transcription terminator. The vector may also contain sequences useful for the amplification of gene expression.

Expression and cloning vectors can, and usually do, contain a selection gene or selection marker. Typically, this gene encodes a protein necessary for the survival or growth of the host cell transformed with the vector. Examples of suitable markers include dihydrofolate reductase (DHFR) or neomycin resistance for eukaryotic cells and tetracycline or ampicillin resistance for *E. coli*. Selection markers in plants include resistance to bleomycin, gentamycin, glyphosate, hygromycin, kanamycin, methotrexate, phleomycin, phosphinotricin, spectinomycin, streptomycin, sulfonamide and sulfonylureas. Maliga et al., *Methods in Plant Molecular Biology*, Cold Spring Harbor Press, 1995, p. 39.

In addition, expression vectors can also contain marker sequences operatively linked to a nucleotide sequence for a protein that encode an additional protein used as a marker. The result is a hybrid or fusion protein comprising two linked and different proteins. The marker protein can provide, for example, an immunological or enzymatic marker for the recombinant protein produced by the expression vector. Suitable markers include, but are not limited to, alkaline phosphatase (AP), myc, hemagglutinin (HA), β-glucuronidase (GUS), luciferase, and green fluorescent protein (GFP).

The polynucleotide sequences of the present disclosure may also be part of an expression cassette that at a minimum comprises, operably linked in the 5' to 3' direction, a regulatory sequence such as a promoter, a polynucleotide encoding a peptide of the present disclosure, and a transcriptional termination signal sequence functional in a host cell. The promoter can be of any of the types discussed herein, for example, a tissue specific promoter, a developmentally regulated promoter, an organelle specific promoter, a seed specific promoter, a plastid specific promoter, etc. The expression cassette can further comprise an operably linked targeting, transit, or secretion peptide coding region capable of directing transport of the protein produced. The expression cassette can also further comprise a nucleotide sequence encoding a selectable marker and/or a purification moiety.

More particularly, the present disclosure includes recombinant constructs comprising an isolated polynucleotide sequence encoding the antifungal peptides of the present disclosure. The constructs can include a vector, such as a plasmid or viral vector, into which the sequence has been inserted, either in the forward or reverse orientation. The recombinant construct can further comprise regulatory sequences, including, for example, a promoter operatively linked to the sequence. Large numbers of suitable vectors and promoters are known to those skilled in the art and are commercially available.

A further embodiment of the present disclosure relates to transformed host cells containing constructs comprising the oligonucleotide sequences of the present disclosure. The host cell can be a higher eukaryotic cell, such as a mammalian or plant cell, or a lower eukaryotic cell such as a yeast cell, or the host can be a prokaryotic cell such as a bacterial cell. Introduction of the construct into the host cell can be accomplished by a variety of methods including calcium phosphate transfection, DEAE-dextran mediated transfection, Polybrene, protoplast fusion, liposomes, direct microinjection into the nuclei, scrape loading, and electroporation. In plants, a variety of different methods can be employed to introduce transformation/expression vectors into plant protoplasts, cells, callus tissue, leaf discs, meristems, etc., to generate transgenic plants. These methods include, for example, *Agrobacterium*-mediated transformation, particle gun delivery, microinjection, electroporation, polyethylene glycol-mediated protoplast transformation, liposome-mediated transformation, etc. (reviewed in Potrykus (1991) *Annu. Rev. Plant Physiol. Plant Mol. Biol.* 42: 205).

Peptides produced by expression of the polynucleotides of the present disclosure can be obtained by transforming a host cell by any of the previously described methods, growing the host cell under appropriate conditions, inducing expression of the polynucleotide and isolating the protein(s) of interest. If the protein in retained within the host cell, the protein can be obtained by lysis of the host cells, while if the protein is a secreted protein, it can be isolated from the culture medium. Several methods are available for purification of proteins and are known to those of ordinary skill in the art. These include precipitation by, for example, ammonium sulfate or ethanol precipitation, acid extraction, anion or cation exchange chromatography, phosphocellulose chromatography, hydrophobic interaction chromatography, affinity chromatography, hydroxylapatite chromatography, lectin chromatography, high performance liquid chromatography (HPLC), electrophoresis under native or denaturing conditions, isoelectric focusing, and immunoprecipitation.

Alternatively, peptides encoded by the polynucleotides of the present disclosure can be produced by chemical synthesis using either solid-phase peptide synthesis or by classical solution peptide synthesis also known as liquid-phase peptide synthesis. In oligomer-supported liquid phase synthesis, the growing product is attached to a large soluble polymeric group. The product from each step of the synthesis can then be separated from unreacted reactants based on the large difference in size between the relatively large polymer-attached product and the unreacted reactants. This permits reactions to take place in homogeneous solutions, and eliminates tedious purification steps associated with traditional liquid phase synthesis. Oligomer-supported liquid phase synthesis has also been adapted to automatic liquid phase synthesis of peptides.

For solid-phase peptide synthesis, the procedure entails the sequential assembly of the appropriate amino acids into a peptide of a desired sequence while the end of the growing peptide is linked to an insoluble support. Usually, the carboxyl terminus of the peptide is linked to a polymer from which it can be liberated upon treatment with a cleavage reagent. In a common method, an amino acid is bound to a resin particle, and the peptide generated in a stepwise manner by successive additions of protected amino acids to produce a chain of amino acids. Modifications of the technique described by Merrifield are commonly used (see, e.g., Merrifield, *J. Am. Chem. Soc.* 96: 2989-93, 1964). In an automated solid-phase method, peptides are synthesized by loading the carboxy-terminal amino acid onto an organic linker (e.g., PAM, 4-oxymethylphenylacetamidomethyl), which is covalently attached to an insoluble polystyrene resin crosslinked with divinyl benzene. The terminal amine may be protected by blocking with t-butyloxycarbonyl. Hydroxyl- and carboxyl-groups are commonly protected by blocking with O-benzyl groups. Synthesis is accomplished in an automated peptide synthesizer, a number of which are commercially available. Following synthesis, the product may be removed from the resin. The blocking groups are removed typically by using hydrofluoric acid or trifluoromethyl sulfonic acid according to established methods (e.g., Bergot and McCurdy, *Applied Biosystems Bulletin,* 1987). Following cleavage and purification, a yield of approximately 60 to 70% is typically produced. Purification of the product peptides is accomplished by, for example, crystallizing the peptide from an organic solvent such as methyl-butyl ether, then dissolving in distilled water, and using dialysis (if the molecular weight of the subject peptide is greater than about 500 daltons) or reverse high-pressure liquid chromatography (e.g., using a C18 column with 0.1% trifluoroacetic acid and acetonitrile as solvents) if the molecular weight of the peptide is less than 500 daltons. Purified peptide may be lyophilized and stored in a dry state until use. Analysis of the resulting peptides may be accomplished using the common methods of analytical high pressure liquid chromatography (HPLC) and electrospray mass spectrometry (ES-MS).

In general, transgenic plants comprising cells containing polynucleotides of the present disclosure can be produced by any of the foregoing methods; selecting plant cells that have been transformed on a selective medium; regenerating plant cells that have been transformed to produce differentiated plants; and selecting a transformed plant that expresses the protein(s) encoded by the polynucleotides of the present disclosure at a desired level. Specific methods for transforming a wide variety of dicots and obtaining transgenic plants are well documented in the literature (Gasser and Fraley, *Science* 244:1293, 1989; Fisk and Dandekar, *Scientia Horticulturae* 55:5, 1993; and the references cited therein).

Successful transformation and plant regeneration have been achieved in a variety of monocots. Specific examples are as follows: asparagus (*Asparagus officinalis*; Bytebier et al. (1987) *Proc. Natl. Acad. Sci. USA* 84: 5345); barley (*Hordeum vulgarae*; Wan and Lemaux (1994) *Plant Physiol.* 104: 37); maize (*Zea mays*; Rhodes et al. (1988) *Science* 240: 204; Gordon-Kamm et al. (1990) *Plant Cell* 2: 603; Fromm et al. (1990) *Bio/Technology* 8: 833; Koziel et al. (1993) *Bio/Technology* 11: 194); oats (*Avena sativa*; Somers et al. (1992) *Bio/Technology* 10: 1589); orchardgrass (*Dactylis glomerata*; Horn et al. (1988) *Plant Cell Rep.* 7: 469); rice (*Oryza sativa*, including indica and japonica varieties; Toriyama et al. (1988) *Bio/Technology* 6: 10; Zhang et al. (1988) *Plant Cell Rep.* 7: 379; Luo and Wu (1988) *Plant Mol. Biol. Rep.* 6: 165; Zhang and Wu (1988) *Theor. Appl. Genet.* 76: 835; Christou et al. (1991) *Bio/Technology* 9: 957); rye (*Secale cereale*; De la Pena et al. (1987) *Nature* 325: 274); sorghum (*Sorghum bicolor*; Cassas et al. (1993) *Proc. Natl. Acad. Sci. USA* 90: 11212); sugar cane (*Saccharum* spp.; Bower and Birch (1992) *Plant J.* 2: 409); tall fescue (*Festuca arundinacea*; Wang et al. (1992) *Bio/Technology* 10: 691); turfgrass (*Agrostis palustris*; Zhong et al. (1993) *Plant Cell Rep.* 13: 1); and wheat (*Triticum aestivum*; Vasil et al. (1992) *Bio/Technology* 10: 667; Weeks et al. (1993) *Plant Physiol.* 102: 1077; Becker et al. (1994) *Plant J.* 5: 299).

In one embodiment, plants are transformed with recombinant polynucleotides encoding the antifungal peptides of the present disclosure which result in the peptides being secreted by the plant. In another preferred embodiment, the antifungal peptides are secreted by the roots of the transformed plant. Plants secreting antifungal peptides can be constructed by the above described methods using expression cassettes which incorporate a secretion sequence that directs secretion of the peptides. Alternatively, plants can be transformed with a nucleotide sequence encoding a fusion protein constructed from the antifungal peptides of the present disclosure and a protein which is normally secreted by the plant. For example, a fusion protein can be produced between an antifungal peptide and the cytokinin oxidase enzyme. Cytokinin oxidase is a protective enzyme that acts to degrade exogenous cytokinins that could interfere with plant growth control. By fusing the antifungal peptides to the region of the cytokinin oxidase gene controlling secretion, the antifungal peptide would be secreted by the transformed plant, thus providing protection from pathogenic fungi.

In another embodiment, before being used to transform plants, fusion proteins containing antifungal peptides can be screened for activity using the phage display method of the present disclosure. In general, a fusion protein can be construction containing, an antifungal peptide; the secretory control portion of a protein, such as cytokinin oxidase; and the pVIII or pIII phage coat protein. Phage displayed fusion proteins so constructed can then be screened using the method of the present disclosure to select those fusion proteins that bind to a target pathogenic fungus and result in alternations which limit pathogenicity.

EXAMPLES

The following examples are intended to provide illustrations of the application of the present disclosure. The following examples are not intended to completely define or otherwise limit the scope of the invention.

Example 1

Materials and Methods for Selection and Characterization of Peptides Using Phage Display Technology 1. Fungal Materials and Inoculum.
Soybean leaves with rust pustules were collected from plants grown either in the field or in greenhouses at the North Florida Research and Education Center (University of Florida) located at Quincy, Fla., and shipped to the Division of Plant Sciences (University of Missouri). There, the infected leaves were handled in the laboratory according to APHIS regulations (APHIS permit 71988). Urediniospores were vacuumed from pustules on leaves using a Cyclone Surface Sampler (Burkard Mfg. Co. Ltd., Rickmansworth, England). These spores were used for initial evaluation of the inhibitory potential of affinity-selected, phage-display peptide clones.

Once soybean rust appeared in southeastern Missouri in 2008, a population of urediniospores was collected from all *P. pachyrhizi* pustules of a single soybean leaf using a Cyclone Surface Sampler. This urediniospore population, MOS-2008, was adjusted to a density of $10^5$ spores per ml water and misted onto 1 to 2 month-old soybean plants in a lighted growth chamber maintained under secure conditions as defined by the Missouri Department of Agriculture. Plants were maintained with a 12-h light/dark cycle at 18 to 20° C. A Honeywell QuickSteam humidifier (Honeywell International, Inc., Morristown, N.J.) was placed in the chamber to maintain relative humidity above 90%. These inoculated plants served as a stock source of *P. pachyrhizi* urediniospores.

To produce inoculum for germination and plant infection studies, MOS-2008 urediniospores were vacuumed from leaves of stock plants, suspended in water, and misted onto detached soybean leaves contained in sealed plastic bags. After 15 h incubation at 25° C., inoculated leaves were removed from the bags, gently blotted dry, and transferred to 15-cm Petri plates containing 1% water agar. Leaves in Petri plates were placed in a growth chamber (model MTR30, Conviron; Winnipeg, Manitoba, Canada) and maintained at 22° C. and 90% RH with a 12-h light/dark cycle (cool white fluorescence lighting; 160 W).

2. Selection of Phage-Display Peptides with Affinity for *P. pachyrhizi* Urediniospores.

A phage-display library, Ph.D.-12 (New England BioLabs Inc., Ipswich, Mass.), was used to develop the peptide-affinity selection protocol. The library consisted of random 12-mer peptides fused to five copies of a minor coat protein (pIII) of M13 phage and expressed at the N-terminus. The concentration of the original library was $1.5 \times 10^{13}$ virons $ml^{-1}$, equivalent to 55 copies of each random peptide sequence per 10 µl of the phage suspension.

Before affinity selection, the Ph.D.-12 library was amplified, purified twice by polyethylene glycol (PEG) precipitation, and re-suspended in water to a concentration of $2.5 \times 10^{14}$ virons $ml^{-1}$. In the affinity-selection procedure, one million urediniospores collected from soybean leaves in Florida were incubated in 1 ml of water for 2.5 h at 22° C. to induce germination. Approximately 75% of urediniospores had germinated by this time. In the first round of affinity selection, $2.0 \times 10^{12}$ bacterial transducing units (TU) of phage (36), equivalent to $3.7 \times 10^{13}$ virons and $1.5 \times 10^4$ copies of each peptide sequence from the amplified library, were added to the germinated urediniospores and incubated for an additional 30 min with gentle shaking. The germinated urediniospore-phage mixture was then centrifuged at 1000×g for 1 minute to separate the urediniospore-bound phage from non-bound phage. The urediniospore-phage pellet was resuspended in 1 ml of water, shaken gently, and centrifuged. After 10 wash cycles, bound phage were eluted from urediniospores by the addition of 200 µl of elution buffer (0.1 N Glycine-HCl, 1 g BSA per liter) at pH 2.2 and incubated for 10 min at 25° C. The resulting affinity-selected phage suspension was neutralized with 40 µl of 1 M Tris-Cl (pH 9.0), and the titer (TU) of an aliquot of the eluate was determined.

The remaining phage were amplified by infecting starved cells of *E. coli* ER2738 (33) and purified twice by PEG-precipitation before final suspension in water.

Phage selection was continued for a total of three affinity-purification and two amplification cycles to enrich the phage pool in favor of peptides with strong binding affinity for germinating urediniospores. In the second and third rounds of affinity selection, the procedure was followed as described above with a modified phage input of $2.0 \times 10^{11}$ rather than $2.0 \times 10^{12}$ TU. Phage eluted from urediniospores in the third (final) round of affinity selection were used to infect *E. coli* ER2738 cells. These cells were plated on LB plates containing 50 mg IPTG and 40 mg×gal per liter. Blue plaques, each containing a single phage clone, were randomly selected for analysis of phage-displayed peptide bioactivity.

3. In Vitro Inhibition of Urediniospore Germination by Phage-Display Peptides.

Representative, affinity-selected, phage-display peptide clones were initially assessed in vitro for the ability to inhibit urediniospore germ tube growth. Two-hundred fifty phage clones, randomly chosen from the final selection round, were amplified by *E. coli* infection, twice purified using PEG-precipitation, and re-suspended in sterile deionized water. Phage concentrations were calculated from UV absorbance measurements as virions $\mu l^{-1}$ (2).

A 25-µl water droplet containing ≈300 non-germinated urediniospores collected from soybean leaves in Florida was incubated on a microscope slide in the presence of a phage clone at a concentration equivalent to $10^{13}$ virions $ml^{-1}$. After 8 h incubation at 22° C., urediniospore germination in the presence of each test clone was compared visually with germination in water alone. Urediniospores were visualized using an Olympus Stereo Zoom Microscope (model SZH; Olympus Optical Co., LTD, Tokyo, Japan) at 50× magnification under transmitted light. Images of germinating urediniospores were captured in random microscope fields with a Spot Insight Color digital camera (Diagnostic Instruments, Inc., Sterling Heights, Mich.). Images were manipulated for viewing using Spot imaging software (version 4.0.3) set up with auto exposure to provide contrast of developing germ tubes against a green background. Comparative germination was assessed in three separate experiments. Phage clones that induced greater than 50% reduction in germ tube length (by visual estimation) compared to growth in water were evaluated in seven additional experiments.

The region of the phage genomes that encoded inserted 12-mer peptides was sequenced. Single-stranded DNA was isolated from the recombinant phage particles of each clone (33) and sequenced from the 3'-end on a Prism 377 automated sequencer (Applied Biosystems, Foster City, Calif.) at the University of Missouri DNA Core facility. Nucleotide sequences were then translated into predicted amino acid sequence.

4. Effect of Phage-Display Peptide Concentration on Urediniospore Germination In Vitro.

The bioactivities of two inhibitory phage-display peptide clones, M13-Sp2 and M13-Sp39, identified in initial assessments were estimated over a range of concentrations including 0.5, 1.0, and $1.5 \times 10^{13}$ virions $ml^{-1}$. As before, a 25-µl water droplet containing ≈300 urediniospores was incubated at 22° C. (4) on a microscope slide in the presence of M13-Sp2 or M13-Sp39 at each concentration. Urediniospores in these and all subsequent experiments were derived from the Missouri population, MOS-2008. Control treatments included urediniospores incubated either in water or an equivalent concentration of phage from an unselected library.

Spore germination and germ tube growth were visualized over time and quantified by image capture and analyses using MetaMorph software (Version 6.2r6, Universal Imaging, Downington, Pa.). Germ tube length was measured using a line scan function based on conversion of image pixels to length. Germ tube length was averaged from 50 randomly selected germinated urediniospores in each image and across four experimental replicates per treatment.

5. Inhibition of Leaf Infection by Phage-Display Peptides.

Young, fully expanded soybean leaves were excised from soybean plants (Williams 82) and placed on 1% water agar in Petri dishes. Two 10-μl droplets of each phage-urediniospore or control treatment, as described for in vitro assessments, were applied to the upper surface of a single leaf. Each droplet contained 50 MOS-2008 urediniospores mixed with either M13-Sp2 or M13-Sp39 at a final concentration of $10^{13}$ virions $ml^{-1}$. Droplet treatments were replicated eight times. Inoculated leaves were incubated for 8 h, a wetness period sufficient to ensure infection (18). Droplets were then rinsed from leaves under running water for 5 min, and the leaf surface was gently blotted dry. Leaves were transferred to Parafilm-sealed Petri dishes and incubated in a growth chamber (model MTR30, Conviron, Winnipeg, Manitoba, Canada) at 22° C. and 90% RH with a 12-h light/dark cycle (cool white fluorescence lighting; 160 W). The percentage of inoculations that produced rust lesions was recorded at 3 to 4 day intervals for 27 days.

6. Protein Scaffold-Display Peptide Construction and Expression in *Pichia pastoris*.

A recombinant version of ZmCKXI (21) was used as a scaffold for display of bioactive peptides, Sp2 and Sp39, identified in initial phage-display peptide clone assessments. This scaffold was shown previously to effectively deliver inhibitory peptides in plant tissues (7). The nucleotide sequences for peptides Sp2 (MLESHAWPPRAI; SEQ ID NO. 1) and Sp39 (YNKPSFQDHSVI; SEQ ID NO: 8) were inserted individually at the 3'-end of the ZmCKXI gene. A stop codon was located immediately after the peptide insertion site. The native N-terminal signal of ZmCKXI was replaced with the a-factor propeptide sequence of *Saccharomyces cerevisiae* (32) to ensure efficient secretion of expressed ZmCKXI-peptide fusions from *P. pastoris* strain X33.

ZmCKX1-Sp2 and ZmCKX1-Sp39 constructs were ligated into the *P. pastoris* cytoplasmic expression vector, pPZICa (Easy Select *Pichia* Expression Kit Version B, Invitrogen, Carlsbad, Calif.). Subsequent transformation and manipulations of *P. pastoris* X33 were performed according to kit instructions. Typically, transformed X33 colonies were selected on Difco Yeast Extract-Peptone-Dextrose Sorbitol (YPDS) medium (Becton Dickinson, Sparks, Md.) amended with 100 μg $ml^{-1}$ zeocin. One confirmed transformed colony from each ZmCKX1-peptide construct was inoculated into Buffered Minimal Glycerol (BMGY) medium (Invitrogen, Carlsbad, Calif.), grown overnight, re-suspended in Buffered Minimal Methanol (BMMH) medium (Invitrogen, Carlsbad, Calif.) containing 0.5% (vol/vol) methanol, and grown at 30° C. with vigorous aeration. Additional methanol was added (0.5%, vol/vol) at 24, 48, and 72 h post-inoculation.

At harvest, culture medium was centrifuged, and the supernatant was cleared by filtration through a 0.22-μm Stericup filter (Millipore, Billerica, Mass.). Recovered medium was concentrated through a Millipore NMWL:30,000 ultrafiltration membrane, and the medium was exchanged with TE buffer (10 mM Tris.Cl, 1 mM EDTA) at pH 8.0 in a stirred-cell filtration apparatus. Purification of protein to greater than 95% electrophoretic homogeneity was achieved by size-exclusion chromatography on Superose 12 (Amersham Pharmacia Biotech, Piscataway, N.J.).

The purified medium containing ZmCKX1-peptide was then passed through an Amicon Ultra-15 filter (Ultracel—30K, Millipore; Billerica, Mass.) and concentrated to 750 μl by centrifugation. Concentrated medium was exchanged four times with 15× volume of sterile, deionized water and re-concentrated. Finally, 750 μl of medium was cleared by filtration through a 0.22-μm syringe filter before assessment of protein concentration, enzyme activity, and bioactivity against *P. pachyrhizi* urediniospores.

Purified ZmCKX1-peptide activity was measured by a continuous dichloroindophenol (DCPIP) reduction assay (1, 15). In a microtiter well, 50 μl of ZmCKX1-SP2 or ZmCKX1-Sp39 was combined with 200 μl of reaction mixture consisting of 250 μM zeatin as substrate and 250 mM sodium phosphate (pH 7.0), 125 μM DCPIP, and 2.5 mM EDTA. A control treatment for each ZmCKX1-peptide included the same reaction mixture, but without zeatin. DCPIP reduction was measured at 590 nm at 10-s intervals for 10 min in a VersaMax (Molecular Devices, Sunnyvale, Calif.) microplate reader and quantified with Softmax Pro 4.3.1 software. Total protein in culture medium was assessed by Bradford assay.

7. In Vitro and in Planta Inhibition of Urediniospore Germination by ZmCKX1-Peptides.

Purified ZmCKX1-Sp2 and ZmCKX1-Sp39 peptides were assessed in vitro for the ability to inhibit urediniospore germination. A 25-μl water droplet containing 300 freshly harvested MOS-2008 urediniospores was incubated on a glass slide in the presence of either ZmCKX1-Sp2 or ZmCKX1-Sp39. Control treatments included urediniospores incubated in water or in the presence of ZmCKX1 alone. Germ tube growth was visualized over time and quantified by image capture and analyses as described previously.

Young, fully expanded leaves were excised from soybean plants (Williams 82) and used for assessment of ZmCKX1-peptide inhibition. Two 10-μl droplets of each ZmCKX1-peptide-urediniospore mixture or control treatment were applied to the upper surface of a single leaf. Each droplet contained 50 urediniospores mixed with either ZmCKX1-Sp2 or ZmCKX1-Sp39 at a final concentration of 115 μM. Control treatments included urediniospores in water or mixed with 115 μM ZmCKX1. Droplet treatments were replicated four times.

Inoculated leaves were incubated for 8 h before rinsing away droplets and drying as described previously. Leaves were transferred to sealed Petri dishes and incubated in a growth chamber at 22° C. and 90% RH, under a 12 h light/dark cycle. The percentage of inoculations that produced rust lesions was recorded at 3 to 4 day intervals for 27 days.

8. Characterization of Protein Targets in Germinating Urediniospores.

A far-western assay was used to identify *P. pachyrhizi* proteins that bind to the disclosed peptides (3, 35). To prepare fungal proteins, MOS-2008 urediniospores were germinated and grown for 4 h. Fungal tissues were ground in liquid nitrogen and suspended in phosphate buffer (pH. 6.5) containing 0.1 M mannitol and Tween-20. Fungal debris was separated from soluble material by centrifugation, and the protein concentration of the soluble fraction was determined. Equal amounts of protein were loaded into the wells of an acrylamide gel, separated by SDS-PAGE, and then transferred to PVDF membrane. The membranes were incubated with a bait protein that consisted of the ZmCKX1 scaffold alone, ZmCKX1-Sp2, or ZmCKX1-Sp39. The unbound bait proteins were washed off of the blot, and the blot was incubated with ZmCKX1 polyclonal antibody (1), followed by a second antibody, anti-rabbit IgG conjugated to alkaline phosphatase (Promega, Madison, Wis.).

Example 2

Phage-Display Peptide Selection and Assessment of Bioactivity

Phage clones from an M13 phage-display library that displayed combinatorial peptides with affinity for germinated urediniospores were isolated. The bioactivity of the enriched phage populations derived from three rounds of selection was then assessed. Out of 250 phage-display peptide clones, 20 peptides were found to reduce urediniospore germ tube growth by 50% or more in at least one of three in vitro trials, at $10^{13}$ virions $ml^{-1}$ (FIG. 1). These bioactive clones and sequenced, and 11 unique inserted peptide sequences (SEQ ID. Nos. 1-11) were identified in these clones, as shown in Table 1. Each of the 11 peptide sequences was re-tested to determine the relative effectiveness of each expressed peptide sequence as germ tube inhibitors. In tests against field-collected urediniospores, phage-display peptide clones inhibited germ tube growth in 30 to 80% of the tests (Table 1). Variation in germ tube inhibition was not surprising given that the field populations of urediniospores used in these initial evaluations likely were heterogeneous in age and viability.

TABLE 1

Sequences of bioactive phage-display peptides that reduced germ tube growth of *P. pachyrhizi* urediniospores[y]

| Name | SEQ ID | Amino-acid sequence | Number of phage-peptide clones recovered | Frequency of germ tube inhibition over 10 trials[z] |
|---|---|---|---|---|
| Sp2 | 1 | MLESHAWPPRAI | 3 | 8 |
| Sp5 | 2 | YISPLPNAATIS | 1 | 3 |
| Sp6 | 3 | TFDRHILDTRGS | 1 | 3 |
| Sp8 | 4 | STVASLGKPTKI | 1 | 4 |
| Sp14 | 5 | ASTIGNLMPGHS | 2 | 5 |
| Sp15 | 6 | FDPHEPTNTRSP | 2 | 6 |
| Sp18 | 7 | LTKEPATGRAML | 4 | 6 |
| Sp39 | 8 | YNKPSFQDHSVI | 2 | 7 |
| Sp51 | 9 | DHIRISTSYKSP | 1 | 3 |
| Sp59 | 10 | TPTRSLDSPHNM | 2 | 4 |
| Sp61 | 11 | DRFTSDLRAPDS | 1 | 3 |

[y]Phage-display peptide clones were recovered from three affinity-selection rounds against germinated urediniospores.
[z]Inhibition was defined as 50% or greater germ tube inhibition after 8 h incubation at 25° C.

As shown in Table 1, the most consistently active phage-display peptides in the enriched population were multiply represented among the 20 clones. The five phage-display peptide clones (Sp2, Sp14, Sp15, Sp18, and Sp39) that inhibited germling growth in 50% or more of 10 trials were represented in the active phage-display peptide population between two and four times. With one exception (peptide Sp59), clones that were least consistently effective at inhibiting germ tube growth were represented only once. None of the phage-display peptide clones that inhibited germling growth significantly inhibited the percentage of urediniospore germination.

Example 3

Figure 2:
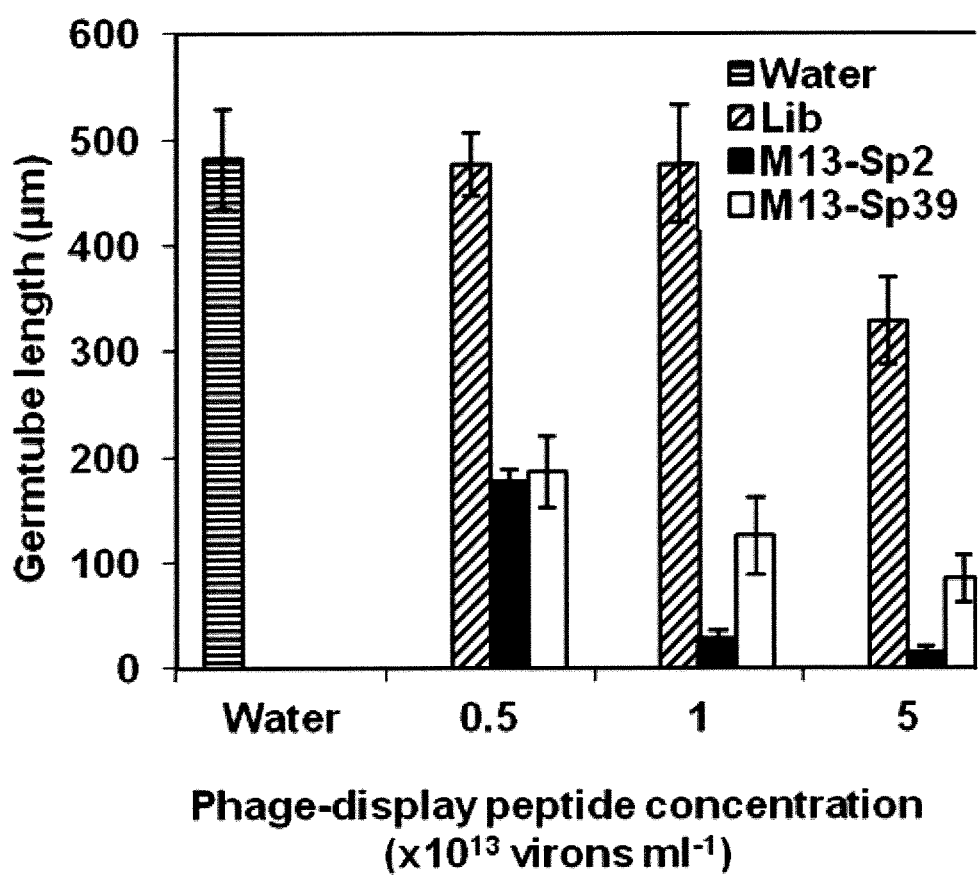

Urediniospore Germ Tube Growth in the Presence of Phage-Display Peptides or ZmCKX1-Peptides The capabilities of the two most consistently active phage-display peptides (M13-Sp2 and M13-Sp39) to inhibit germ tube growth were further characterized. After 8 h incubation, the average germ tube length in water was 482 µm. Both clones inhibited growth during this time period in a concentration-dependent fashion (FIG. 2). In comparison to growth in water, the average length of urediniospore germ tubes was reduced by 62-64% in the presence of either phage-display peptide clone at a concentration of $5 \times 10^{12}$ virions $ml^{-1}$. Germ tube inhibition increased with higher virion concentrations to a maximum of 97% and 82% for M13-Sp2 and M13-Sp39, respectively, at a concentration of $5 \times 10^{13}$ virions $ml^{-1}$. Germ tube growth in the presence of the unselected phage-display peptide library was not inhibited in comparison to growth in water (<1.5%), except at the highest concentration of $5 \times 10^{13}$ virions $ml^{-1}$, where growth inhibition was 32%.

Figure 3:
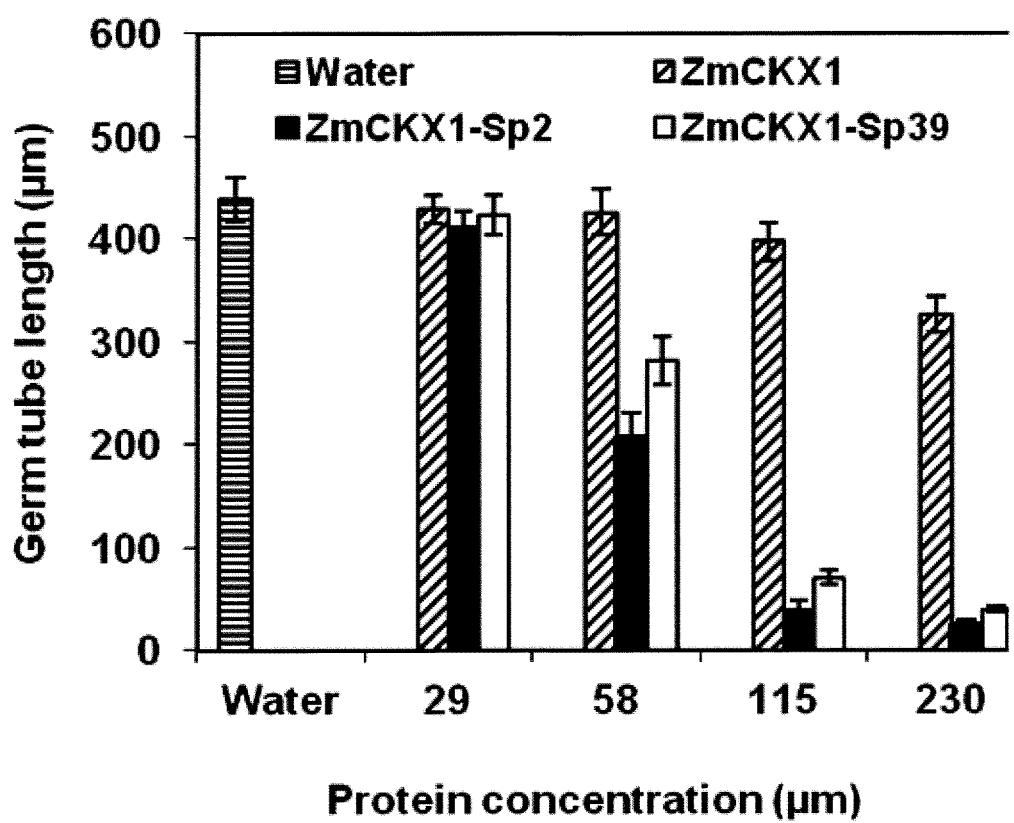

When peptides Sp2 and Sp39 were fused to the C-terminus of the scaffold protein, ZmCKX1, they also inhibited urediniospore germination in vitro in a concentration-dependent fashion (FIG. 3). In these experiments, after 8 h incubation the average germ tube length in water was 438 µm. In comparison to water, significant reductions in germ tube growth were detected at ZmCKX1-peptide concentrations of 58 µM or greater. At 58 µM ZmCKX1-Sp2 and ZmCKX1-Sp39, the average length of urediniospore germ tubes was reduced by 52% and 36%, respectively. At the highest concentration of 230 µM ZmCKX1-Sp2 or ZmCKX1-Sp39, germ tube growth was decreased by 94% and 91%, respectively. Germ tube growth in the presence of ZmCKX1 alone was inhibited less than 10% at all concentrations except 230 µM, where 26% growth inhibition was detected.

Example 4

Figure 4:
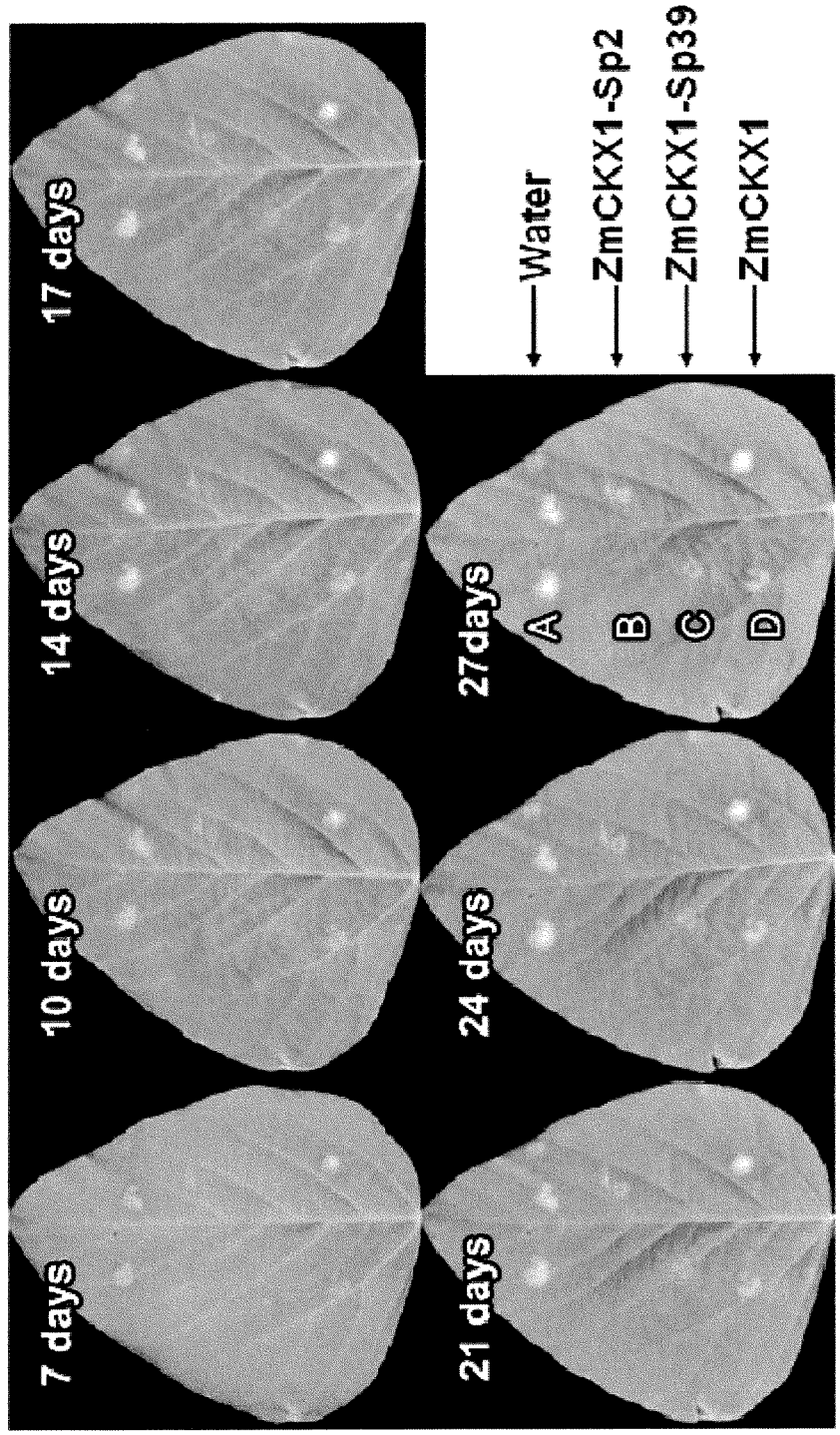
Figure 5:
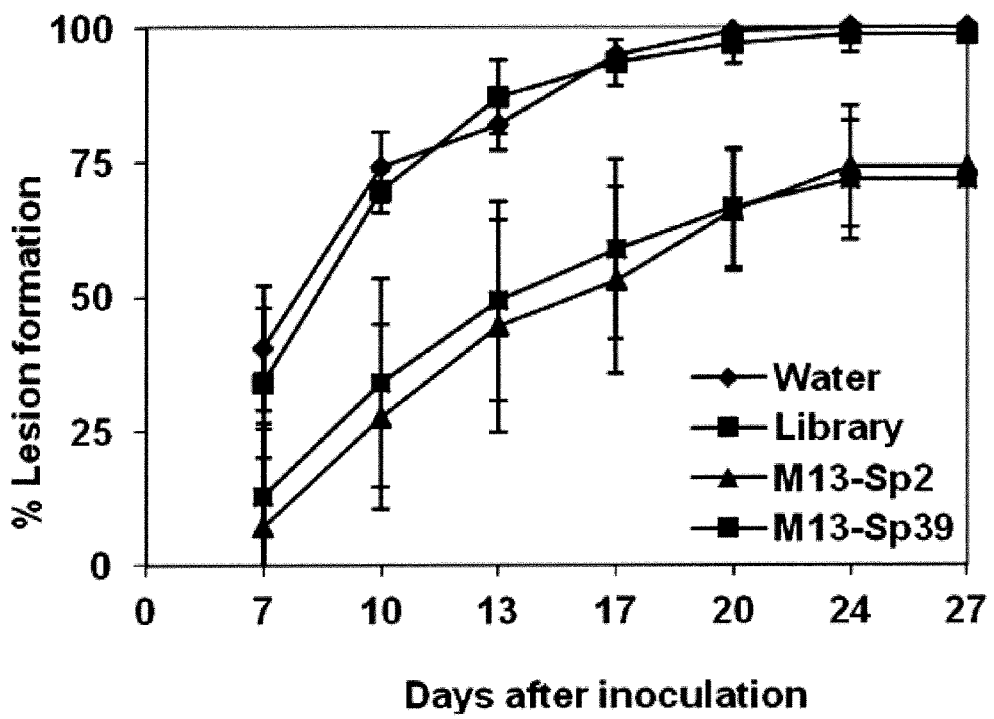
FIG. 5 shows the influence of phage-display peptides on rust lesion formation after leaf inoculation with *Phakopsora pachyrhizi* urediniospores.

Inhibition of *P. pachyrhizi* Leaf Infection by Phage-Display Peptides or ZmCKX1-Peptides Peptides Sp2 and Sp39, when displayed on phage or as fusions with ZmCKX1, inhibited rust lesion development on soybean leaves inoculated with urediniospores (FIG. 4). Two replicate inoculations of each treatment were made per leaf. Leaf wetness was maintained for 8 h before blotting dry and subsequent incubation for 27 days. Fifty urediniospores in 10 µl water were inoculated to leaf surfaces and incubated for 8 h before drying which generated visible lesions after 7 days of additional incubation (FIG. 5). Leaves were inoculated with 50 urediniospores mixed with 10 µl of $10^{13}$ virions $ml^{-1}$ of phage-display peptides, M13-Sp2 and M13-Sp39, with the unselected phage-display peptide library, or water as controls. Leaf wetness was maintained for 8 h before blotting dry. Bars indicate standard error of the mean (n=8). An average of about 40% of these inoculations produced lesions by that time. In comparison, only 7% and 12% of the urediniospore inoculations produced lesions when phage-display peptides, M13-Sp2 or M13-Sp39, were added to the inoculum. By 13 days after inoculation, an average of 82% of inoculations with urediniospores in water produced visible lesions, whereas lesion formation was reduced to 44 and 49% by M13-Sp2 or M13-Sp39, respectively. Although all inoculations with urediniospores in water produced lesions by 24 days, fewer than 75% of inoculations in the presence of either peptide ever produced lesions.

Figure 6:
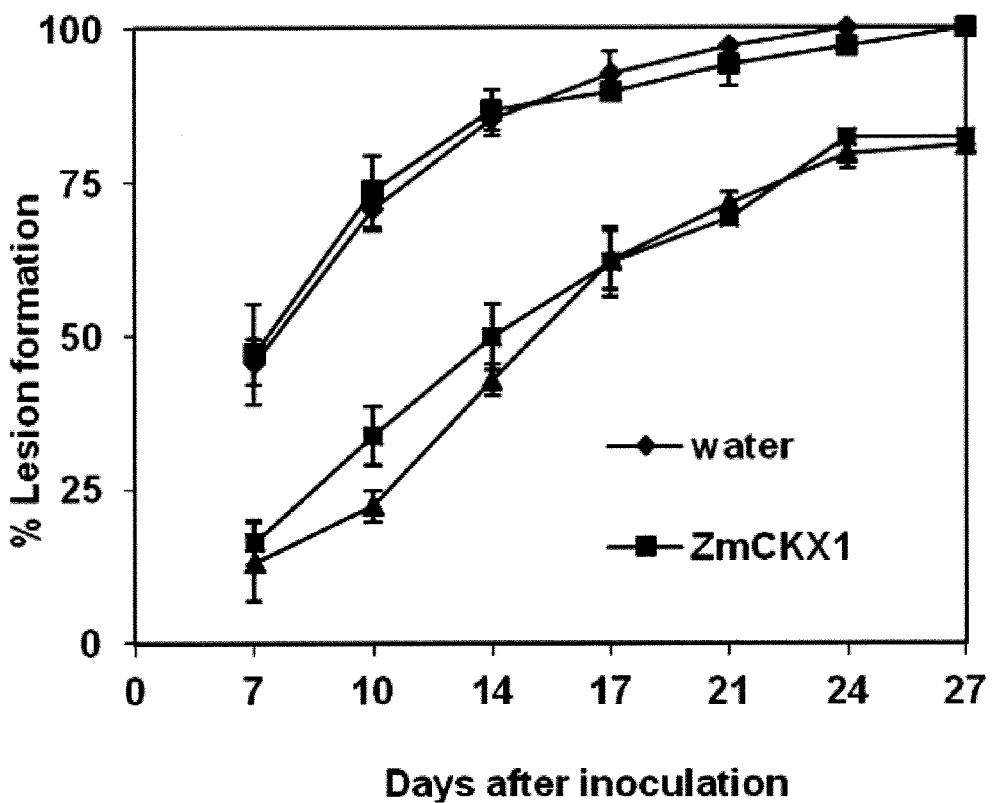
FIG. 6 shows the influence of scaffold-display peptides on rust lesion formation after inoculation with *Phakopsora pachyrhizi* urediniospores.

Similar reductions were observed in lesion formation on soybean leaves inoculated with urediniospores mixed with scaffold-peptides (FIG. 6). Leaves were inoculated with 50 urediniospores mixed with 10 µl of 115 µM scaffold-display peptides, ZmCKX1-Sp2 and ZmCKX1-Sp39, with 115 μM ZmCKX1 without peptide insert, or water. Leaf wetness was maintained for 8 h before blotting dry. Bars indicate standard error of the mean (n=8). Although close to 50% of urediniospores inoculated to leaves in water had produced lesions after 7 days of incubation, lesion formation was reduced to 13% and 16%, respectively, by the ZmCKX1-Sp2 and ZmCKX1-SP39 preparations. By day 24, whereas a maximum of 74% of inoculations in the presence of scaffold-peptides produced lesions, all urediniospores inoculated in water produced lesions. The results indicate that the peptides were growth-inhibitory but not fungicidal, an observation consistent with the in vitro activity of the peptides fused to either carrier phage or to ZmCKX1 (FIG. 2 and FIG. 3).

Example 5

Detection of Protein Targets on the Pathogen that Bind to Peptides SP20R SP39

FIG. 7 shows results of an experiment to identify the protein targets on the pathogen that binds to the peptides. Protein extracted from germinated urediniospores was separated by SDS-PAGE and transferred to a PVDF membrane before incubation with either A, ZMCKX1, B, ZMCKX1-Sp2, or C, ZMCKX1-Sp39 protein, followed by successive treatments with ZmCKX1 antibody and anti-rabbit IgG conjugated to alkaline phosphatase. The arrow on the right illustrates the 20 kDa fungal protein band. Arrows on the left indicate the sizes of protein standards. Scaffold-display peptides, ZmCKX1-Sp2 and ZMCKX1-Sp39, specifically interacted with a fungal protein approximately 20 kDa in size (FIG. 7). Significantly, this protein was absent in the blot probed with the ZMCKX1 scaffold, indicating that the Sp-2 and Sp-39 peptides were responsible for its detection. Because both the Sp-2 and Sp-39 peptides appeared to bind to the same 20 kDa protein, these results suggest that these peptides either target the same sequence or they may target different sequences on the same protein.

Example 6

Use of Cytokinin Oxidase (CKX) as a Protein Scaffold for Delivery of the Defense Peptides to Points of Fungal Infection in Bean (*Phaseolus vulgaris*) Tissues A construct containing a coding sequence encoding one or more of the defense peptides (also referred to as "anti-fungal peptides" or "bioactive peptides") (such as SEQ ID Nos. 1-11) and a coding sequence encoding one or more of the scaffold proteins is built. This construct is introduced into bean (*Phaseolus vulgaris*) where a fusion protein containing the defense peptides fused with the scaffold proteins such as CKX. CKX is modified as described above and in U.S. Pat. No. 7,700,831 to fuse with the anti-fungal peptides. An *agrobacterium*-mediated transformation of *Phaseolus vulgaris* is performed to provide a plant expressing the fusion protein. The transformed plants are exposed to *U. appendiculatus* or *Phakopsora pachyrhizi*. The rate and severity of infection are compared to a control plant to confirm efficacy of the defense peptides against the pathogen.

Transgenic plants showing enhanced resistance to infection by one or more of the pathogenic fungi may be selected for planting in regions where such fungal infection has been reported or in regions that are likely to be invaded by these pathogenic fungi.

Example 7

Use of Cytokinin Oxidase as a Protein Scaffold for Delivery of Defense Peptides to Points of Fungal Infection in Soybean (*Glycine Max*) Tissues A construct containing a coding sequence encoding one or more of the defense peptides (such as those of SEQ ID Nos. 1-11) and a coding sequence encoding one or more of the scaffold proteins is built. This construct is introduced into soybean (*Glycine max*) where a fusion protein containing one or more defense peptides fused with one or more scaffold proteins such as CKX. CKX is modified as described above and in U.S. Pat. No. 7,700,831 to fuse with the anti-fungal peptides. An *agrobacterium*-mediated transformation of *Glycine max* is performed to provide a plant expressing the fusion protein.

Detailed description of soybean transformation is provided in Hiei et al., 1997, *Plant Mol. Biol.* 35:205-218; Komari T., 1990, *Plant Cell Rep.* 9: 303-306; Ishida et al., 1996, *Nature Biotechnol.* 14:745-750; Zhao et al., 1999, U.S. Pat. No. 5,981,840; Zhao et al., 2004, U.S. Pat. No. 6,822,144; Zhao et al, 2000, *Plant Mol. Biol.* 44:789-798; and Zeng et al., 2004, *Plant Cell Rep.* 22:478-482, as well as in U.S. patent application Ser. No. 12/023,237. The transformed plants are exposed to *U. appendiculatus* or *Phakopsora pachyrhizi*. The rate and severity of infection are compared to a control plant to confirm efficacy of the defense peptides against the pathogen.

Transgenic soybean plants showing enhanced resistance to infection by one or more of the pathogenic fungi may be selected for planting in regions where such fungal infection has been reported or in regions that are likely to be invaded by these pathogenic fungi.

LITERATURE CITED

The following documents are quoted in the text by a number within parenthesis. These documents and all other references cited in this disclosure are hereby incorporated by reference to the same extent as though fully reproduced herein.

1. Bilyeu, K. D., Cole, J. L., Laskey, J. G., Riekhof, W. R., Esparza, T. J., Kramer, M. D., and Morris, R. O. 2001. Molecular and biochemical characterization of a cytokinin oxidase from maize. Plant Physiol. 125:378-386.
2. Bishop-Hurley, S. L., Mounter, S. A., Laskey, J., Morris, R. O., Elder, J., Roop, P., Rouse, C., Schmidt, F. J., and English, J. T. 2002. Phage-displayed peptides as developmental agonists for *Phytophthora capsici* zoospores. Appl. Env. Microbiol. 68:3315-3320.
3. Bishop-Hurley, S. L., Schmidt, F. J., and Smith, A. L. 2005. Peptides selected for binding to a virulent strain of *Haemophilus influenzae* by phage display are bactericidal. Antimicrob. Agents Chemotherapy 49:2972-2978.

4. Bonde, M. R., Berner, D. K., Nester, S. E., and Frederick, R. D. 2007. Effects of temperature on urediniospore germination, germ tube growth, and initiation of infection in soybean by *Phakopsora* isolates. Phytopathology 97:997-1003.
5. Bonde, M. R., Melching, J. S., and Bromfield, K. R. 1976. Histology of the suscept-pathogen relationship between *Glycine max* and *Phakopsora pachyrhizi*, the cause of soybean rust. Phytopathology 66:1290-1294.
6. Christiano, R. S. C., and Scherm, H. 2007. Quantitative aspects of the spread of Asian soybean rust in the southeastern United States, 2005 to 2006. Phytopathology 97:1428-1433.
7. Fang, D. F., Laskey, J. G., Huang, S., Bilyeu, K. D., Morris, R. O., Schmidt, F. J., and English, J. T. 2006. Combinatorially selected defense peptides protect plant roots from pathogen infection. PNAS 103:18444-18449.
8. Hartman, G. L., Miles, M. R., and Frederick, R. D. 2005. Breeding for resistance to soybean rust. Plant Dis. 89:664-666.
9. Hennings, V. P. 1903. A few new Japanese Uredinaceae. Hedwigia 42:S107-108.
10. Isard, S. A., Dufault, N. S., Miles, M. R., Hartman, G. L., Russo, J. M., De Wolf, E. D., and Morel, E. 2006. The effect of solar irradiance on the mortality of *Phakopsora pachyrhizi* urediniospores. Plant Dis. 90:941-945.
11. Jurick, W. M., II, Navaraez, D. F., Brennan, M. M., Harmon, C. L., Marois, J. J., Wright, D. L., and Harmon, P. F. 2008. Winter survival of the soybean rust pathogen, *Phakopsora pachyrhizi*, in Florida. Plant Dis. 92:1551-1558.
12. Koch, E., Ebrahim-Nesbat, F., and Hoppe, H. H.1983. Light and electron microscopic studies on the development of soybean rust (*Phakopsora pachyrhizi* Syd.) in susceptible soybean leaves. Phytpathol. Z. 106:302-320.
13. Koch, E., and Hoppe, H. H.1988. Development of infection structures by the direct-penetrating soybean rust fungus (*Phakopsora pachyrhizi* Syd.) on artificial medium. J. Phytopathol. 122:232-244.
14. Krupa, S., Bowersox, V., Claybrooke, R., Barnes, R., Szabo, C. W., Harlin, K., and Kurle, J. 2006. Introduction of Asian soybean rust urediniospores into the Midwestern United States—a case study. Plant Dis. 90:1254-1259.
15. Laskey, F. G., Patterson, P., Bilyeu, D., and Morris, R. O. 2003. Rate enhancement of cytokinin oxidase/dehydrogenase using 2,6-dichlorophenol as an electron acceptor. Plant Growth Reg. 40:189-196.
16. Lygin, A. V., Li, S., Vittal, R., Widholm, J. M., Hartman, G. L., and Lozovaya, V. V. 2009. The importance of phenolic metabolism to limit the growth of *Phakopsora pachyrhizi*. Phytopathology 99:1412-1420.
17. Marchetti, M. A., Uecker, F. A., and Bromfield. 1976. The effects of temperature and dew period on germination and infection by uredospores of *Phakopsora pachyrhizi*. Phytopathology 66:461-463.
18. Melching, J. S., Dowler, W. M., Koogle, D. L., and Royer, M. H.1989. Effects of duration, frequency, and temperature of leaf wetness periods on soybean rust. Plant Dis. 73:117-122.
19. Miles, M. R., Levy, C., Morel, W., Mueller, T., Steinlage, T., van Rij, N., Frederick, R. D., and Hartman, G. L. 2007. International fungicide efficacy trials for the management of soybean rust. Plant Dis. 91:1450-1458.
20. Miles, M. R., Pastor-Corrales, M. A., Hartman, G. L., and Frederick, R. D. 2007. Differential response of common bean cultivars to *Phakopsora pachyrhizi*. Plant Dis. 91:698-704.
21. Morris, R. O., Bilyeu, K. D., Laskey, J. G., and Cheikh, N. N. 1999. Isolation of a gene encoding a glycosylated cytokinin oxidase from maize. Biochem. Biophys. Res. Commun. 255:328-333.
22. Mortel, -M.-van-de, Recknor, J. C., Graham, M. A., Nettleton, D., Dittman, J. D., Nelson, R. T., Godoy, C. V., Abdelnoor, R. V., Almeida, A., M. R., and Baum, T. 2007. Distinct biphasic mRNA changes in response to Asian soybean rust infection. Mol. Plant-Microbe Interact. 20:887-899.
23. Mueller, T. A., Miles, M. R., Morel, W., Marois, J. J., Wright, D. L., Kemerait, R. C., Levy, C., and Hartman, G. L. 2009. Effect of fungicide and timing of application on soybean rust severity and yield. Plant Dis. 93:243-248.
24. Panthee, D. R., Marois, J. J., Wright, D. L., Narváez, D., Yuan, J. S., and Stewart, C. N., Jr. 2009. Differential expression of genes in soybean in response to the causal agent of Asian soybean rust (*Phakopsora pachyrhizi* Sydow) is soybean growth stage-specific. Theor. Appl. Genet. 118:359-370.
25. Panthee, D. R., Yuan, J. S., Wright, D. L., Marois, J. J., Mailhot, D., and Stewart, C. N., Jr. 2007. Gene expression analysis in soybean in response to the causal agent of Asian soybean rust (*Phakopsora pachyrhizi* Sydow) in an early growth stage. Funct. Integr. Genomics 7:291-301.
26. Pimental, D., Zuniga, R., and Morrison, D. 2005. Update on the environmental and economic costs associated with alien-invasive species in the United States. Ecol. Econ. 52:273-288.
27. Pivonia, S., and Yang, X. B. 2004. Assessment of the potential year-round establishment of soybean rust throughout the world. Plant Dis. 88:523-529.
28. Pivonia, S., and Yang, X. B. 2005. Assessment of epidemic potential of soybean rust in the United States. Plant Dis. 89:678-682.
29. Posada-Buitrago, M. L., and Frederick, R. D. 2005. Expressed sequence tag analysis of the soybean rust pathogen, *Phakopsora pachyrhizi*. Fungal Gen. Biol. 42:949-962.
30. Rossman, A. Y. 2009. The impact of invasive fungi on agricultural ecosystems in the United States. Biol. Invasions 11:7-101.
31. Schneider, R. W., Hollier, C. A., Whitam, H. K., Palm, M. E., McKenny, J. M., Hernández, J. R., Levy, L., and DeVries-Paterson, R. 2005. First report of soybean rust caused by *Phakopsora pachyrhizi* in the continental United States. Plant Dis. 89:774.
32. Scorer, C. A., Buckholz, R. G., Clare, J. J., Romanos, M. A. 1993. The intracellular production and secretion of HIV-1 envelope protein in the methylotrophic yeast *Pichia pastoris*. Gene 136:111-119.
33. Smith, G. P., and Scott, J. K. 1993. Libraries of peptides and proteins displayed on filamentous phage. Methods Enzymol. 217:228-257.
34. Sydow, H., and Sydow, P. 1914. A contribution to knowledge of the parasitic fungi of the island of Formosa. Annal. Mycol. 12:105.
35. Wu Y., Li Q., and Chen X. 2007. Detecting protein-protein interactions by far western blotting. Nature Protocols. 2:3278-3284.
36. Yu, J., and Smith, G. P. 1996. Affinity maturation of phage-displayed peptide ligands. Methods Enzymol. 267:3-27.

We claim:

1. A transgenic plant comprising a transgene formed of a polynucleotide, wherein said polynucleotide comprises a first DNA fragment encoding a first polypeptide comprising SEQ ID NO: 1 and a second DNA fragment encoding a second polypeptide facilitating the presentment of said first polypeptide to a pathogen, wherein said second polypeptide is a cytokinin oxidase (CKX) or a coat protein of M13 phage.

2. The transgenic plant of claim 1, wherein said transgenic plant is generated by introducing said polynucleotide into a host plant by transformation, said host plant being susceptible to infection by a fungus selected from the group consisting of *Uromyces appendiculatus*, *Phytophthora capsici*, and *Phakopsora pachyrhizi.*

3. The transgenic plant of claim 2, wherein said host plant is a soybean plant.

4. The transgenic plant of claim 2, wherein said transgenic plant is more resistant than said host plant to infection caused by at least one fungus selected from the group consisting of *Uromyces appendiculatus, Phytophthora capsici*, and *Phakopsora pachyrhizi.*

5. The transgenic plant of claim 1, wherein said second polypeptide being in the same molecule as said first polypeptide when said polynucleotide is expressed in said plant.

6. The transgenic plant of claim 1, wherein said polynucleotide further encodes a third polypeptide comprising an amino acid sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and combinations thereof.

7. The transgenic plant of claim 6, wherein said third polypeptide comprises SEQ ID NO: 8.

8. A polynucleotide comprising a first DNA fragment encoding a first polypeptide comprising SEQ ID NO: 1, the polynucleotide residing in an expression vector.

9. The polynucleotide of claim 8, further comprising a second DNA fragment encoding a second polypeptide, said second polypeptide being in the same molecule as said first polypeptide when said polynucleotide is expressed in a plant, wherein said second polypeptide facilitates the presentment of said first polypeptide to a pathogen, wherein said second polypeptide is a cytokinin oxidase (CKX) or a coat protein of M13 phage.

10. The polynucleotide of claim 9, wherein said polynucleotide further encodes a third polypeptide comprising an amino acid sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and combinations thereof.

11. A polypeptide comprising SEQ ID NO: 1.

12. The polypeptide of claim 11, wherein said polypeptide further comprises an additional amino acid sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and combinations thereof.

13. A vector comprising the polynucleotide of claim 8.

14. A cell comprising the polynucleotide of claim 8.

15. A method for conferring fungal resistance upon a host plant, said host plant being susceptible to fungal infection, said method comprising:
(a) introducing into said host plant a polynucleotide to obtain a transgenic plant, said polynucleotide comprising a first DNA fragment encoding a first polypeptide comprising SEQ ID NO: 1 and a second DNA fragment encoding a second polypeptide facilitating the presentment of said first polypeptide to a pathogen, wherein said second polypeptide is a cytokinin oxidase (CKX) or a coat protein of M13 phage; and
(b) allowing said first and second polypeptides to be expressed in said transgenic plant, wherein said transgenic plant is more resistant than said host plant to fungal infection.

16. The method of claim 15, wherein said host plant is a soybean plant.

17. The method of claim 15, wherein said transgenic plant is more resistant than said host plant to infection caused by at least one fungus selected from the group consisting of *Uromyces appendiculatus, Phytophthora capsici*, and *Phakopsora pachyrhizi*.

18. The method of claim 15, said second polypeptide being in the same molecule as said first polypeptide when said polynucleotide is expressed in said host plant.

19. The method of claim 15, wherein said polynucleotide further encodes a third polypeptide comprising an amino acid sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and combinations thereof.

20. The method of claim 15, wherein said third polypeptide comprises SEQ ID NO: 8.

21. The transgenic plant of claim 1, wherein said CKX is a modified CKX.

22. The polynucleotide of claim 9, wherein said CKX is a modified CKX.

23. The method of claim 15, wherein said CKX is a modified CKX.

* * * * *

SEQUENCE LISTING

<160> NUMBER OF SEQ ID NOS: 11

<210> SEQ ID NO 1
<211> LENGTH: 12
<212> TYPE: PRT
<213> ORGANISM: Artificial Sequence
<220> FEATURE:
<223> OTHER INFORMATION: Random peptide insert

<400> SEQUENCE: 1

Met Leu Glu Ser His Ala Trp Pro Pro Arg Ala Ile
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Random peptide insert

<400> SEQUENCE: 2

Tyr Ile Ser Pro Leu Pro Asn Ala Ala Thr Ile Ser
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Random peptide insert

<400> SEQUENCE: 3

Thr Phe Asp Arg His Ile Leu Asp Thr Arg Gly Ser
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Random peptide insert

<400> SEQUENCE: 4

Ser Thr Val Ala Ser Leu Gly Lys Pro Thr Lys Ile
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Random peptide insert

<400> SEQUENCE: 5

Ala Ser Thr Ile Gly Asn Leu Met Pro Gly His Ser
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Random peptide insert

<400> SEQUENCE: 6

Phe Asp Pro His Glu Pro Thr Asn Thr Arg Ser Pro
1               5                   10

```
<210> SEQ ID NO 7
<211> LENGTH: 12
<212> TYPE: PRT
<213> ORGANISM: Artificial Sequence
<220> FEATURE:
<223> OTHER INFORMATION: Random peptide insert

<400> SEQUENCE: 7

Leu Thr Lys Glu Pro Ala Thr Gly Arg Ala Met Leu
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Random peptide insert

<400> SEQUENCE: 8

Tyr Asn Lys Pro Ser Phe Gln Asp His Ser Val Ile
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Random peptide insert

<400> SEQUENCE: 9

Asp His Ile Arg Ile Ser Thr Ser Tyr Lys Ser Pro
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Random peptide insert

<400> SEQUENCE: 10

Thr Pro Thr Arg Ser Leu Asp Ser Pro His Asn Met
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Random peptide insert

<400> SEQUENCE: 11

Asp Arg Phe Thr Ser Asp Leu Arg Ala Pro Asp Ser
1               5                   10
```